(12) United States Patent
Vassarotti et al.

(10) Patent No.: US 6,837,995 B1
(45) Date of Patent: Jan. 4, 2005

(54) DEVICE FOR CONCENTRATING AND PURIFYING MACROMOLECULES

(75) Inventors: Vincenzo Vassarotti, deceased, late of Rolle (CH); by Salvatore Aversano, legal representative, Geneva (CH)

(73) Assignee: Vivascience AG, Hannover (DE)

( * ) Notice: Subject to any disclaimer, the term of this patent is extended or adjusted under 35 U.S.C. 154(b) by 0 days.

(21) Appl. No.: 09/913,781

(22) PCT Filed: Feb. 8, 2000

(86) PCT No.: PCT/EP00/00976
§ 371 (c)(1),
(2), (4) Date: Jun. 12, 2002

(87) PCT Pub. No.: WO00/48716
PCT Pub. Date: Aug. 24, 2000

(30) Foreign Application Priority Data

Feb. 15, 1999 (SE) .............................. 9900530

(51) Int. Cl.⁷ .............................................. B01D 63/00
(52) U.S. Cl. ......................... 210/321.84; 210/321.75; 210/321.6; 422/101; 422/102
(58) Field of Search ................. 210/650, 781, 210/380.1, 787, 360.1, 361, 477, 321.75, 321.6, 321.84; 422/72, 101, 102; 436/177, 45

(56) References Cited

U.S. PATENT DOCUMENTS 3,583,627 A * 6/1971 Wilson ........................ 494/36
4,948,564 A * 8/1990 Root et al. ................... 422/101
5,647,990 A * 7/1997 Vassarotti .................... 210/650

* cited by examiner

*Primary Examiner*—W. L. Walker
*Assistant Examiner*—K S Menon
(74) *Attorney, Agent, or Firm*—Chernoff, Vilhauer, McClung & Stenzel, LLP (57) ABSTRACT

A device for concentrating and/or purifying macromolecules in liquids is disclosed wherein the concentration/purification is accomplished by a membrane separating concentration and filtration chambers, the membrane and chambers being compressively held in fluid-tight relationship by sliding engagement with a sleeve-like housing. A method for assembling such a device is also disclosed.

4 Claims, 8 Drawing Sheets

Fig. 15

DEVICE FOR CONCENTRATING AND PURIFYING MACROMOLECULES

This is a 371 of PCT/EP00/00976, filed Feb. 08, 2000, and claims priority of the Swedish Application No. 9900530-8, filed Feb. 15, 1999.

BACKGROUND OF THE INVENTION

Many biotechnology laboratories and health care institutions use micro- and ultrafiltration methods for processing biological solutions. Examples include the use of such filtration to remove bacteria, to remove suspended solids and contaminants, to concentrate proteins and other macromolecules and to eliminate unwanted micromolecules such as salts.

Centrifugal forces, gas or liquid pressure or vacuum are typically used as the driving force to push or pull solvent and small micromolecules through the membrane while solute components larger than the molecular weight cut-off of the membrane are retained on the feed side of the membrane as retentate or concentrate. In most applications, the higher the pressure or vacuum exerted, the higher is the rate of filtration relative to the membrane surface area used. In general, high speed and small surface area membranes are preferred.

Typical such devices include a chamber for the sample to be processed and a chamber for the capture of the permeate/filtrate, the two chambers being in fluid communication through at least one common aperture across which a membrane such as a microporous ultrafiltration or reverse osmosis membrane is arranged. The membrane is typically sealed fluid-tight at its periphery to the surface at the periphery of the aperture of either the processing/concentration chamber or the permeate chamber, or to both.

The membrane is usually reinforced on its permeate side to withstand transmembrane pressure. There is a feed inlet provided for introducing a liquid sample to the concentration chamber and an outlet for the filtrate from the filtrate chamber. In so-called tangential flow devices there is an additional outlet provided in the concentration chamber to permit recirculation of the liquid sample.

The sealing of the membrane to the filtration device must meet very high requirements so that the liquid to be processed is prevented from by-passing the membrane. The membrane may be sealed in a variety of ways such as by heat-sealing, adhesive- or solvent-bonding, ultrasonic welding or by an interference fit. In addition, material and wall thickness for the chambers which are also sealed together are chosen in order to withstand the operating pressure. Such devices are sometimes also provided with separate pressure holders or membrane assemblies placed between external pressure plates, which are typically bolted together to provide additional support.

One of the problems with such prior art devices is the difficulty in obtaining a satisfactory compromise between, on the one hand, seal reliability for both the membrane and/or for the joint between the chambers to provide adequate pressure containment and, on the other hand, low manufacturing cost.

For practicality and cost reasons, it is desirable to mold such filtration devices but it is not always possible to mold membrane support sections of sufficient thickness to withstand high operating pressures because it is difficult to mix thick and thin areas when molding. The alternative of using separate pressure holders or external pressure plates is both expensive and inconvenient for small devices. Also, although sealing systems that perform well at low to moderate pressures are frequently unreliable at higher pressures.

Another problem is achieving a sufficiently strong seal between the chambers, particularly with incompatible or non-sealing materials and in large surface area devices that must withstand higher overall pressures.

The design of one such centrifugal filtration device is described in U.S. Pat. No. 5,647,990, which discloses a half cylindrical sleeve to retain the filtration membrane in place over the aperture between the concentration and filtrate chambers. A principal drawback of that design is its potential for damaging the relatively fragile membrane when the retaining sleeve is pushed over the concentration chamber, since the resultant frictional forces tend to push the membrane out of alignment with the aperture. Another drawback of said design is that pressure containment and seal integrity are limited by the difficulty of molding a sufficiently thick membrane support plate and the incomplete support provided to the sealing area of the membrane due to permeate outlet passages that directly cross the seal area. The problems caused by frictional forces on the membrane and incomplete seal support are further exacerbated when the membrane is not first sealed to the concentration chamber, but sealing and assembly rather are effected in a single operation by compression during application of the perimeter of the membrane to the aperture of the concentration chamber.

UK Application No. 9819686.8 discloses a so-called tangential flow filtration device. The drawback of this device is the need to machine its component parts due to the difficulty of molding them sufficiently thick to contain high pressures. In addition, relatively expensive bolting mechanisms are required to hold the assembled device together sufficiently tightly to resist high operating pressures.

One object of the present invention is to provide a device of the type mentioned above which is simple to manufacture while providing increased overall reliability.

A further object is to provide a device for which it is possible to choose materials for the retentate and permeate compartments which do not require heat or ultrasonic seal compatibility with each other nor with the membrane used.

A further object is to provide a device which has a supported seal around the entire periphery of the membrane.

A further object of the invention is to provide a device which is possible to reopen and reclose, after processing in order to inspect and/or replace the membrane without damaging the retentate or permeate compartments or the membrane.

A still further object is to provide a method according to which the membrane will be sealed to the filtration device during assembly in a single operation.

The foregoing objects, uses and advantages of this invention will become apparent from the following description.

BRIEF SUMMARY OF THE INVENTION

The invention provides a device for concentrating and/or purifying macromolecules in solution and a method for manufacturing such a device. The device comprises a processing/concentration chamber for the sample to be processed and a chamber for filtrate that is separated by at least one membrane and more specifically provides a novel method of fixing the membrane in a pressure-resistant sealing relationship in the interface between the two chambers. Such devices may be used in centrifuges, as tangential flow modules, as gas-pressurized cells or with hand-operated syringes.

DETAILED DESCRIPTION OF THE INVENTION

Figures 1, 2, 3:
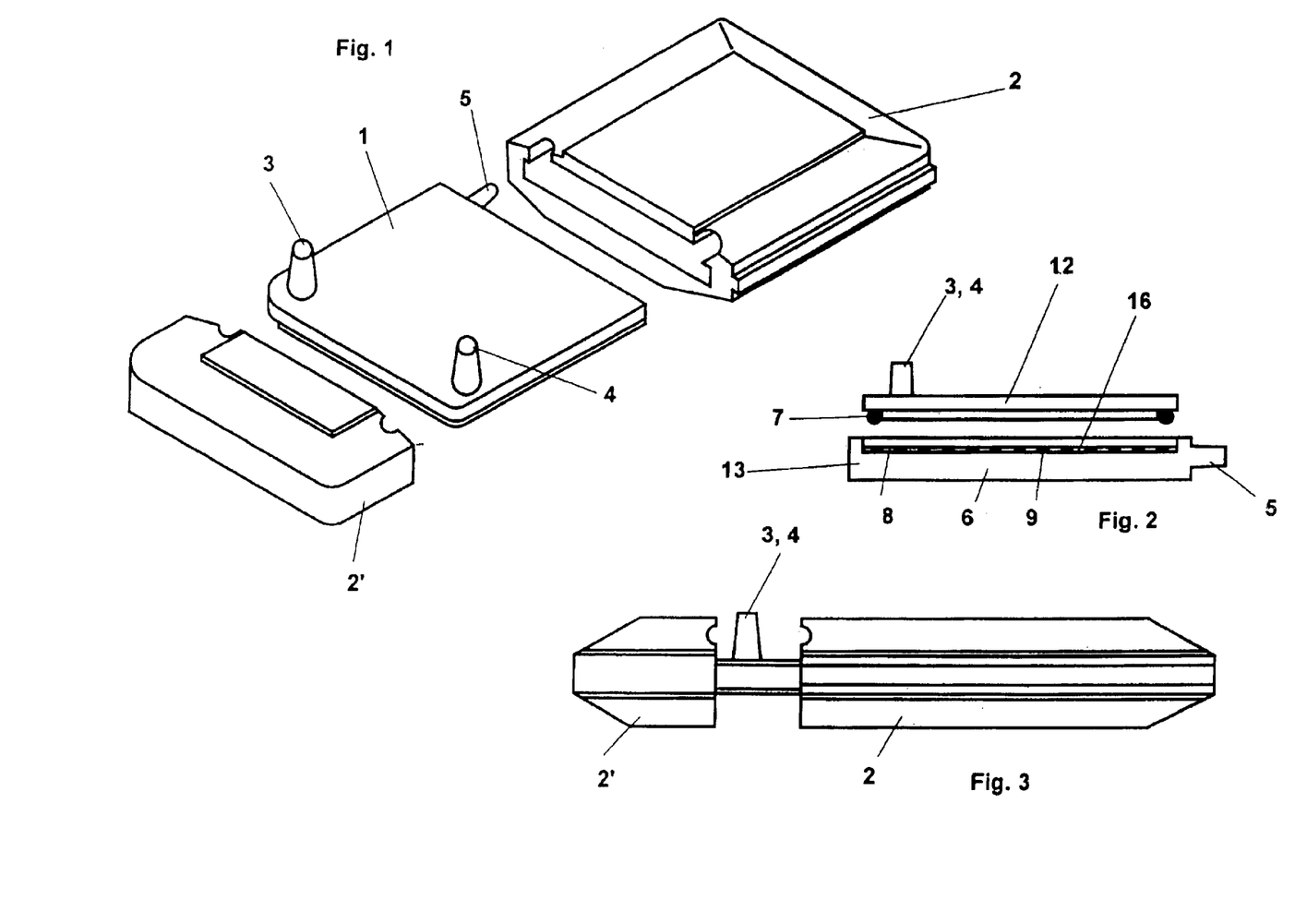
FIG. 1 is a perspective view of an exemplary device of the present invention in the form of a tangential flow module.
FIG. 2 is a cross-sectional view of the filtration insert portion of the device shown in FIG. 1.
FIG. 3 is a side view of the device shown in FIG. 1.

Referring now to the drawings, wherein the same numerals generally refer to like elements, there is shown in FIG. 1 an exploded perspective view of a device according to the present invention in the form of a tangential flow filtration module or cell which can be used, for example, for concentrating and/or fractionating macromolecules in a liquid. In a filtration system this type of filtration module is connected to a pump that typically draws liquid from a reservoir of liquid sample material and pumps it through the module and recirculates liquid sample through a loop that includes the module. The module is incorporated into and in fluid communication with this loop via feed inlet 3 and permeate outlet 4 arranged on filtration insert 1. The necessary system pressure is created by a flow restrictor (not shown) positioned at permeate outlet 4 of the cell.

Figure 5:
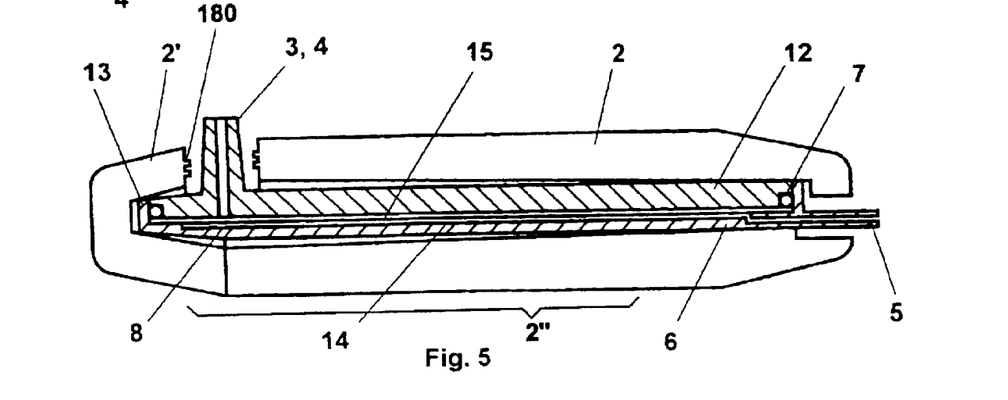
FIG. 5 is a cross-sectional view of the assembled device shown in FIG. 4.
Figure 6:
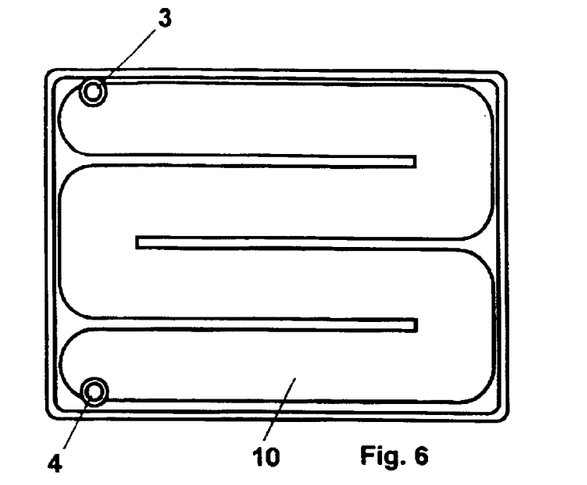
FIG. 6 is a plan view of an upper portion of the filtration insert portion of the device shown in FIG. 1.
Figure 7:
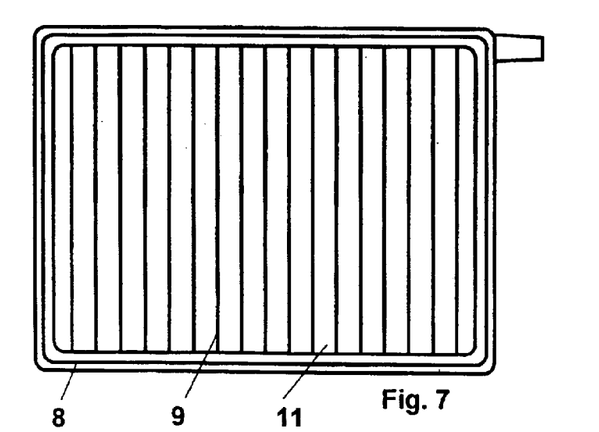
FIG. 7 is a plan view of a lower portion of the filtration insert portion of the device shown in FIG. 1.

As shown in FIGS. 3 and 6–7 filtration insert 1 comprises a concentration (retentate) chamber 10 in the exemplary form of a thin channel (FIG. 6) situated in upper plate 12 (FIG. 2) of insert 1. Filtrate (permeate) chamber 11 (FIG. 7) is situated in membrane support plate 6 (FIG. 2) of filtration insert 1. Concentration and filtrate chambers 10 and 11 are separated from each other by membrane 15 (see FIG. 5).

Due to the pressure difference between the feed side and the permeate side of membrane 15, filtrate permeates through membrane 15 and filtrate chamber 11 and exits via discharge port 5 for collection outside the cell.

FIG. 2 shows in section an exemplary filtration insert 1. Membrane support plate 6 has a generally planar upper surface that functions as a membrane support 16. Membrane support 16 is provided with a plurality of parallel grooves forming filtrate channels 9 for the collection of filtrate, also shown in FIG. 7. Filtrate channels 9 are all in fluid communication with each other by means of transverse outlet channel 14 (shown in FIG. 5), that connects the end portions of filtrate channels 9 on one side of the filtration insert 1 in order to feed all the collected filtrate to discharge port 5.

As shown in FIG. 5, membrane 15 is positioned on top of membrane support 6 of filtration insert 1 and extends to the vertical walls 13 of membrane support 6. Along the inner side of vertical walls 13 a generally flat gasket seat 8 is arranged (see FIGS. 2, 5, 7), making for a generally flat support for membrane 15 all around its periphery. Gasket 7, in the form of an O-ring in this embodiment, is arranged on top of membrane 15 over gasket seat 8 and upper plate 12 closes the filtration insert 1.

A two-part sleeve 2, 2', preferably manufactured by molding a suitable polymer, surrounds filtration insert 1. In the embodiment shown in FIGS. 1 and 3–5 the two-part sleeve 2,2' slidingly engages filtration insert 1 from opposing sides to form the complete sleeve housing 2" and compresses insert 1 without any frictional forces on membrane 15, thereby forming, in a single step, and without the use of any adhesives, bolts or tools, the concentration and filtrate chambers 10 and 11 by sealing the periphery of membrane 15. An additional advantage of the module's construction is that it is easy to take apart for inspection, to change the membrane, for cleaning or for any other purpose without damaging any of its component parts.

FIG. 3 shows a side view of the embodiment shown in FIG. 1. The sliding introduction of filtration insert 1 into the two sleeve parts 2 and 2' starts very easily due to the tapered cross-section of the sleeve and insert, best seen in FIG. 5. Greater force is only needed at the end of the assembly during compression of gasket 7. Sleeve parts 2, 2' and insert 1 may also be assembled by heating sleeve parts 2, 2' before assembly and allowing them to cool.

Figure 4:
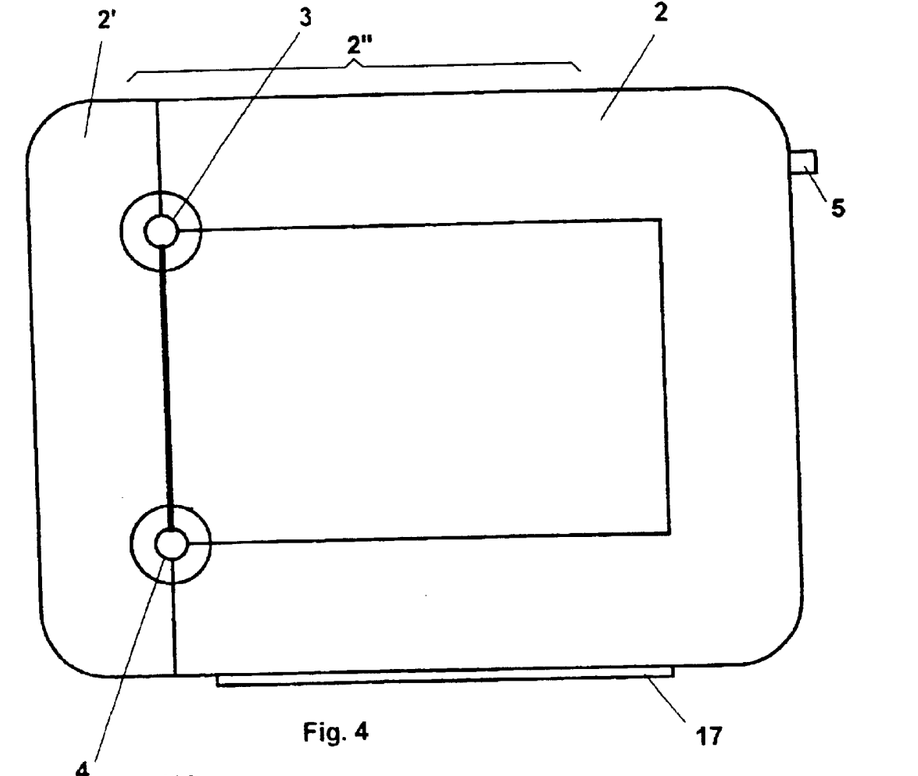
FIG. 4 is a plan view of the device shown in FIG. 1, as assembled.

FIG. 4 is a plan view of the assembled embodiment shown in FIG. 1. In the lower portion of FIG. 4 there is shown attached to sleeve 2 a longitudinal flange 17 adapted to matingly engage a corresponding slot at the upper portion of an adjacent module (not shown), thereby permitting a series of filtrating modules oriented on their edges to be stacked on top of each other.

Figure 8:
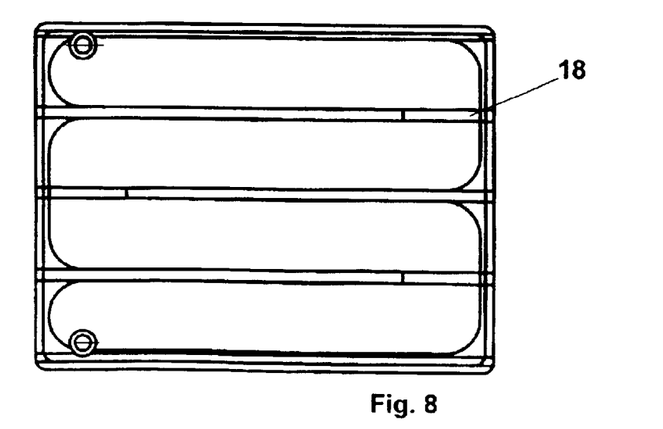
FIG. 8 is a plan view of a modification of the upper portion of the device shown in FIG. 6.

FIG. 5 shows in section the assembled device shown in FIG. 4. As noted above, the insides of the two-part sleeve 2, 2' are tapered. In addition to being practical for manufacturing purposes, tapering permits the achievement of the necessary collaborating compressive forces for filtration insert 1, the exterior of which has a corresponding taper. In order to achieve nearly the same compressive forces but with lower friction between sleeve housing 2" and filtration insert 1 the top and bottom surfaces of filtration insert 1 could be made parallel and the tapered form could be realized by means of longitudinal tapered flanges on the top and bottom surfaces of at least one of them; such an arrangement is illustrated in FIG. 8, showing tapered flanges 18.

An additional advantage to molding the sleeve housing 2" in two parts 2, 2' is that a standardized thread 180 may readily be formed during molding, the thread accommodating feed inlet 3 and permeate outlet 4.

Figure 9:
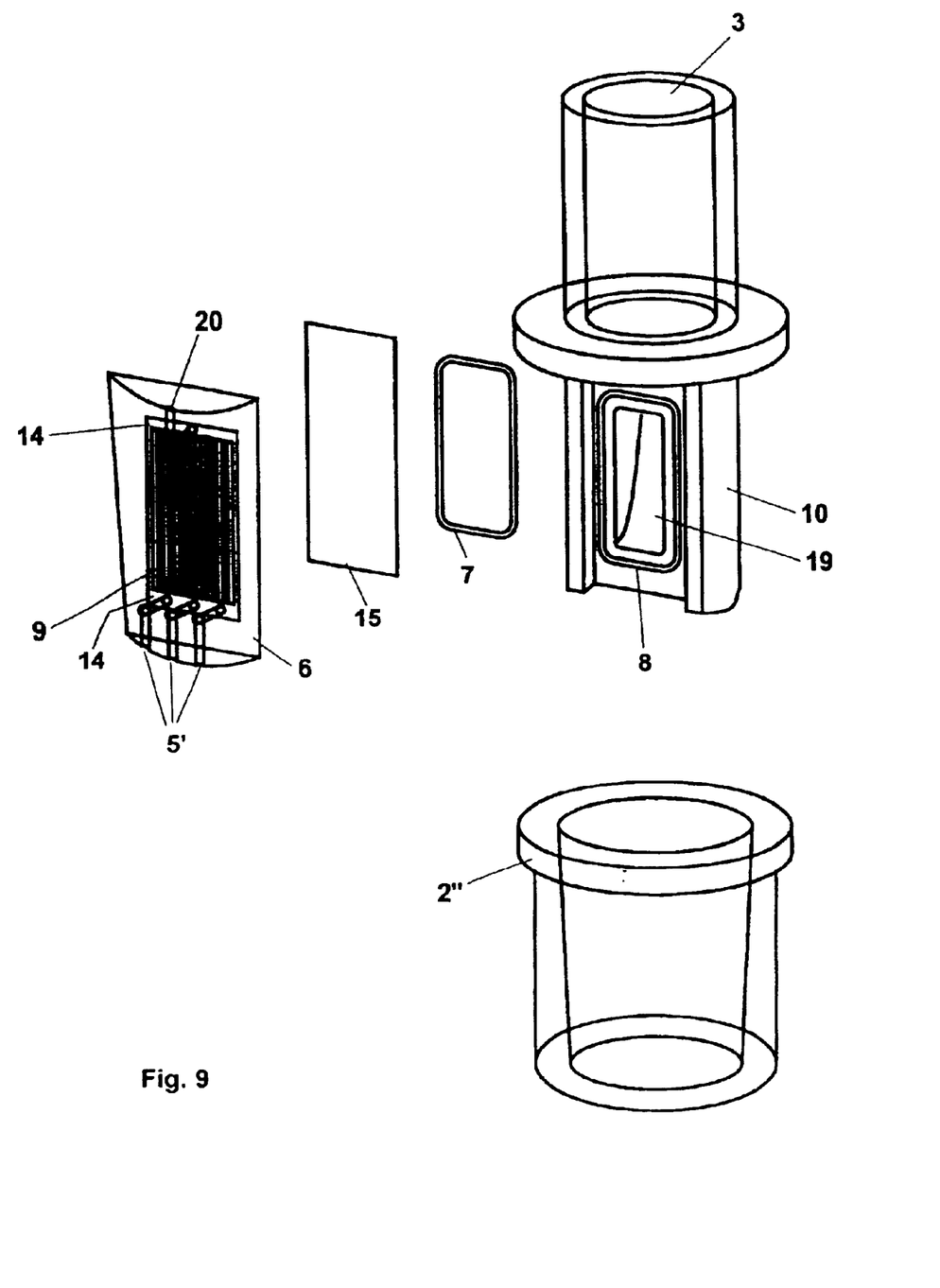
FIG. 9 is an exploded perspective view of another exemplary embodiment of the present invention in the form of a centrifugal filtration device.

FIG. 9 shows an exploded perspective view of another embodiment of the device according to the invention in the form of a centrifugal filtration device. Concentration chamber 10 is provided for receiving the liquid sample to be processed. In this case the sample is not recirculated and so no outlet for the sample is provided therefrom, there being only a feed inlet 3. Gasket 7 is positioned in gasket seat 8 around aperture 19 in the wall of concentration chamber 10. A suitable membrane 15 is positioned over aperture 19. As described above in connection with the embodiment shown in FIG. 1, a filtrate chamber is provided with a membrane support plate 6, gasket seat 8 and a plurality of parallel grooves forming filtrate channels 9 for collection of the filtrate are created when support plate 6 is fixed against membrane 15. Transverse outlet channel 14 is in fluid communication with filtrate channels 9 and with discharge ports 5'. Gas bleed 20 is provided to permit air or gas to escape from filtrate channels 9 prior to filtration.

Figure 10:
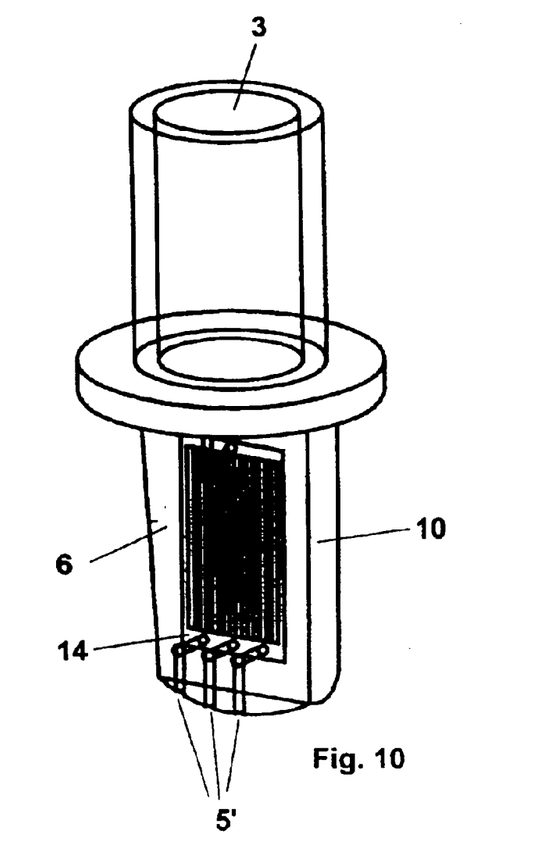
FIG. 10 is an exploded perspective view of the device shown in FIG. 9 illustrating its assembly.
Figure 11:
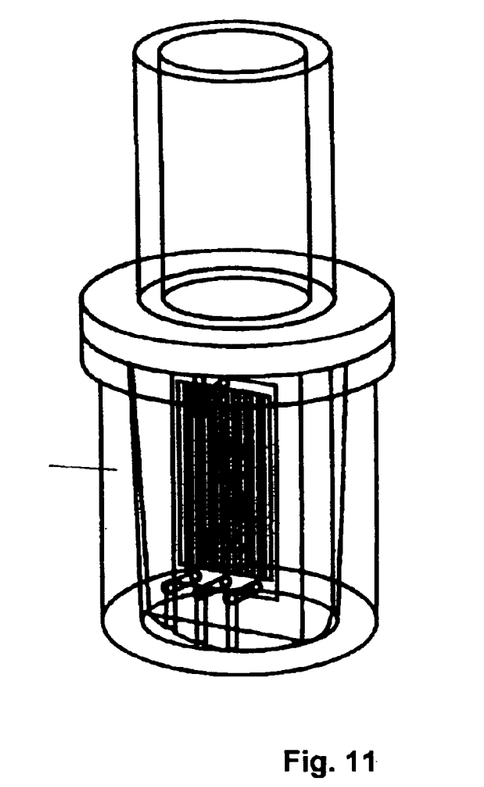
FIG. 11 is a perspective view of the device shown in FIG. 9, fully assembled.

FIG. 10 shows the device of FIG. 9 partially assembled after the components 10, 17, 15 and 6 (shown in FIG. 9) are assembled; a one-piece sleeve housing 2" slidingly engages those assembled components in this embodiment, shown in FIG. 11. Due to the tapered or conical form of the assembled filtrate chamber and the corresponding female portion of sleeve housing 2" the filtrate chamber is forced against membrane 15 and compresses gasket 7 against concentration chamber 10. It should be noted that membrane 15 will only be exposed to forces perpendicular to its surface when sleeve housing 2" is in place. In this way a pressure sufficiently high to seal the membrane fluid-tight against concentration chamber 10 is created and will be maintained during centrifugation.

Figure 12A:
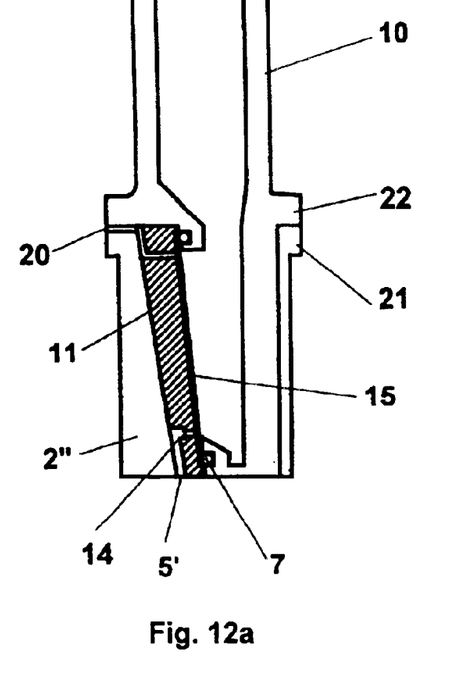
FIG. 12a is a cross-sectional view of the assembled device shown in FIG. 11.

FIG. 12a shows in section the assembled device shown in FIG. 11. At the upper part of concentration chamber 10 gas bleed 20 is in fluid communication with the outside, which may be utilized to evacuate air from filtrate channels 9 at the start of the filtration process. In this embodiment three discharge ports 5' are provided for the discharge of filtrate, to be collected in a filtrate recovery tube (not shown), in which the device is inserted. Discharge ports 5' are in fluid communication with transverse outlet channel 14 as in the embodiment shown in FIG. 5, connecting the end portions of filtrate channels 9 on one side of the filtrate compartment in order to feed all the filtrate collected to discharge ports 5'. The device is supported on flange 21 of sleeve housing 2" against flange 22 of concentration chamber 10, which means that the centrifugal forces acting on the device during centrifugation maintain sleeve housing 2" in position with flange 21 abutting flange 22.

Figure 12B:
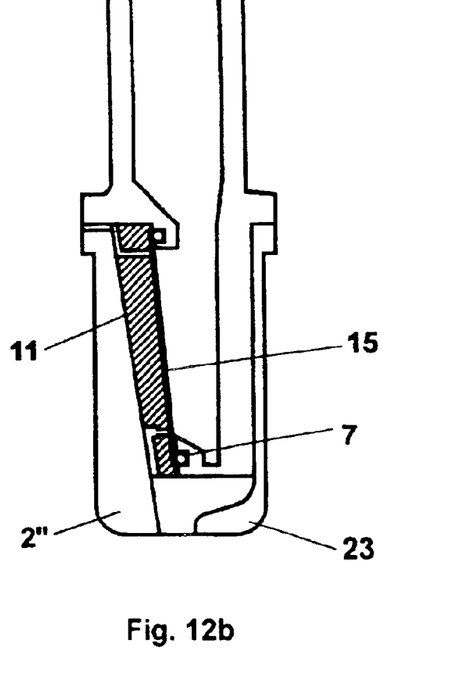
FIG. 12b is a cross-sectional view of the assembled device shown in FIG. 11 provided with a variant of the sleeve component of that device.

FIG. 12b shows in section the assembled device shown in FIG. 11 provided with a variant of sleeve housing 2". In order to ensure sealing between gasket 7 and membrane 15 at the lower part of the device, sleeve housing 2" has been made less flexible in this area by the addition of a stabilizing ring 23 of material around the opening in the lower portion of sleeve housing 2". Stabilizing ring 23 can alternatively have a more flat configuration than the one shown in FIG. 12b. As filtrate channels 9 do not fall below the transverse outlet channel 14 in this embodiment it is possible to arrange a generally flat support for the permeate side of membrane 15 along its periphery, which will ensure a sealing effect all around.

Figure 13A:
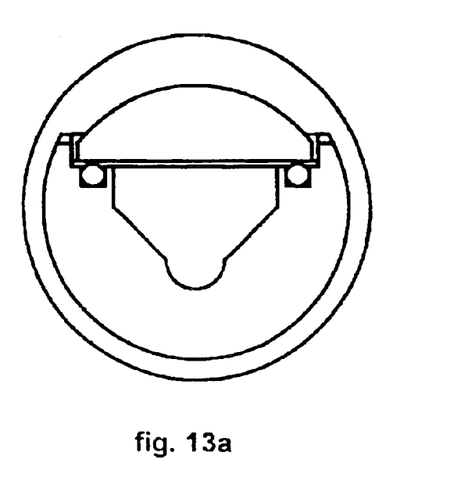
FIGS. 13a and 13b are two horizontal cross-sectional views taken through the assembled device shown in FIG. 12a and 12b, respectively.
Figure 13B:
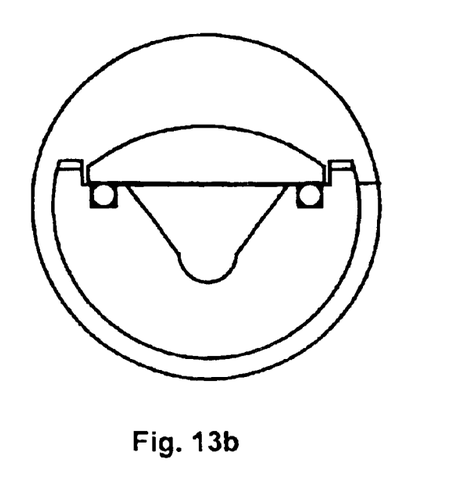

FIGS. 13a and 13b show horizontal sections through the assembled device shown in FIG. 12a at its upper and lower portions, respectively, whereby the tapered form of the membrane support plate 6 is clearly illustrated.

Figure 14:
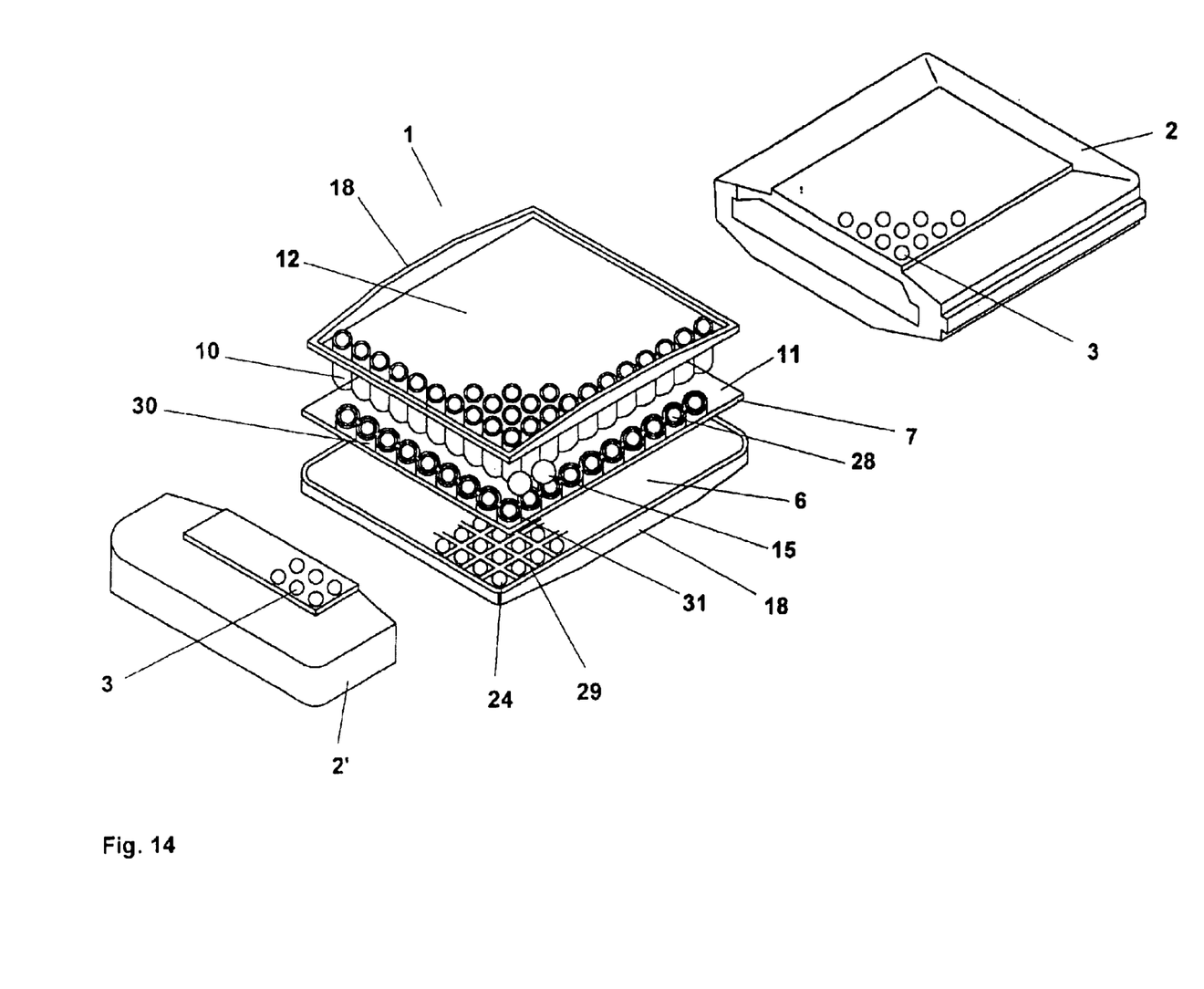
FIG. 14 is an exploded perspective view of an exemplary device of the present invention adapted for the filtration of multiple, samples.
Figure 15:
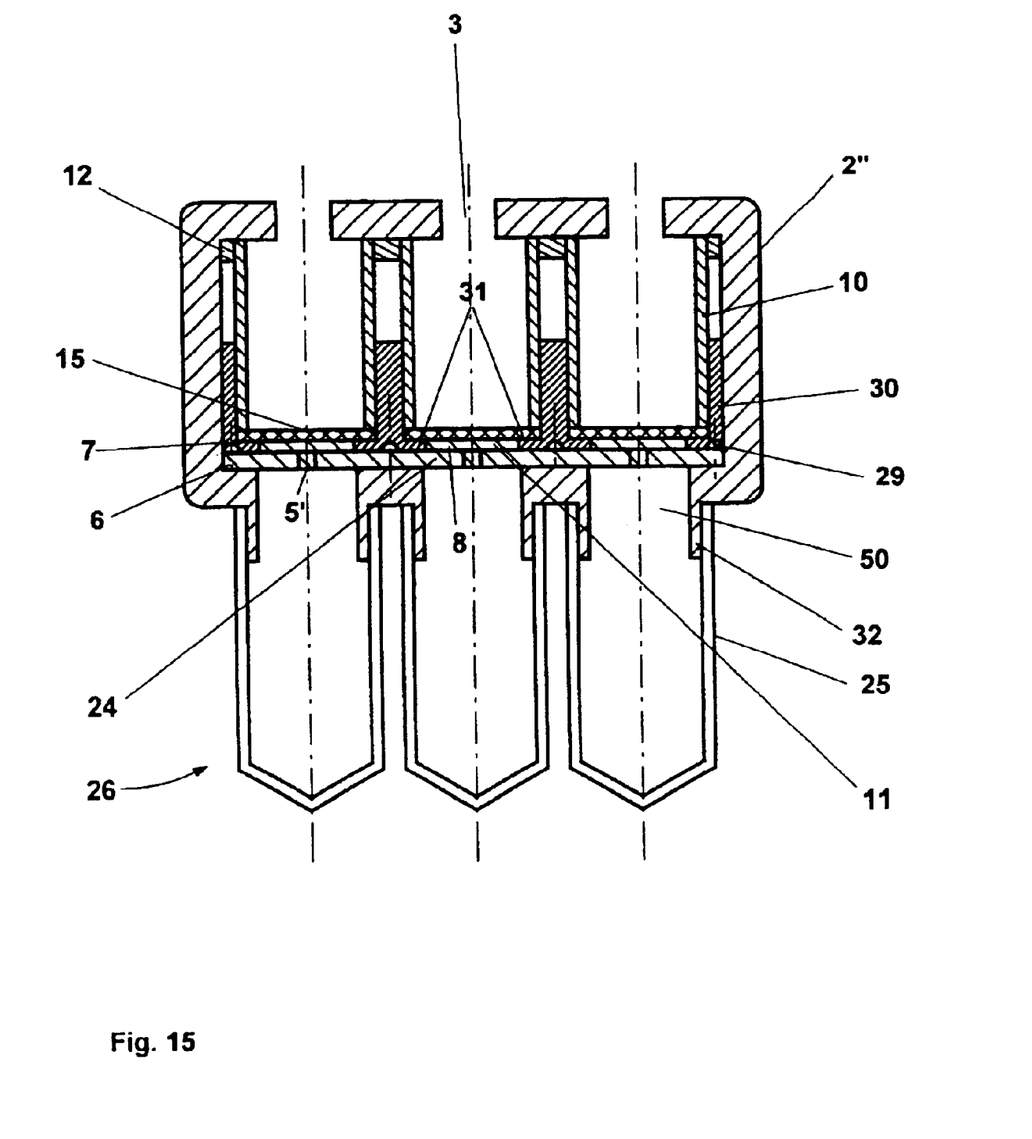
FIG. 15 is a cross-sectional view of the device shown in FIG. 14.

Yet another exemplary embodiment of the invention, for the simultaneous filtration of multiple liquid samples, is depicted in FIGS. 14 and 15 wherein there is shown a filtration insert 1 housed in a two-part sleeve 2, 2'. Filtration insert 1 comprises membrane support plate 6, gasket mat 7, a plurality of flat circular membranes 15 and upper plate 12 with a plurality of tubular concentration chambers 10 and tubular filtrate chambers 11. Tubular filtrate chambers 11 comprise tubular walls 30, circumferential flange 31 and openings 28.

Membrane support plate 6 includes a plurality of openings 24 therein which, in their number and arrangement, preferably correspond to the number and arrangement of receptacles 25 of a micro titer plate 26. Openings 24 in support plate 6 can also be provided with a filter support, which in turn is in fluid communication with collection channels 8 and discharge ports 5' for the discharge of filtrate through filtrate port 50. It should be noted that collection chambers 8 are coextensive with the interior of filtrate chambers 11. Gasket mat 7 is laid upon support plate 6 and has tubular filtrate chamber openings 28 aligned with and corresponding to the number of openings 24 in support plate 6. For easy positioning of gasket mat 7 on support plate 6 and for a more secure sealing of membrane 15 against filtrate chambers 11, partitions or webs 29 are installed surrounding openings 24 in support plate 6.

The tubular walls 30 of filtrate chambers 11 have a larger inner diameter than that of openings 28 and are sized so that walls 30 may be provided with a circumferential sealant flange 31 constructed of sealant material. During assembly, circular membranes 15 are laid on the circumferential sealant flanges 31 of tubular walls 30 and tubular concentration chambers 10 are inserted within tubular walls 30, with tubular concentration chambers 10 being open on both ends and connected to upper plate 12. The outer circumferential surfaces of tubular concentration chambers 10 are congruent with the inner surfaces of tubular walls 30. Tubular concentration chambers 10 serve in the first instance to receive liquid samples to be processed, and secondly to function in cooperation with gasket mat 7 to form a fluid-tight peripheral seal of membranes 15 between sealant flanges 31 and the lower open ends of tubular chambers 10. Tubular walls 30 of tubular filtrate chambers 11 are pushed sufficiently far into tubular concentration chambers 10, that their lowermost portions press against the periphery of membranes 15. The two-part housing 2, 2', is provided with feed inlets 3 on the upper side to receive the liquid samples, and on the underside with discharge ports 5' for the filtrate, which outlets are aligned with openings 24 in support plate 6.

During assembly of the apparatus, the sleeves 2, 2' are pushed over the filtration insert 1 to form housing 2". As this is done, sufficient compressive forces are created and maintained to hold membranes 15 fluid-tight against flanges 31. To this end filtration insert 1 preferably has a conical outer profile, and housing 2" has a corresponding conical inner profile, which two profiles upon fitting together, cooperate to create the necessary compressive forces. As shown in FIG. 14, support plate 6 and upper plate 12 are provided with lateral, wedge-shaped flanges 18.

As shown in FIG. 15, when housing 2" is closed, inlets 3 on the upper side of the housing align with the ends of tubular concentration chambers 10 through filtrate chamber openings 28, with openings 24 in support plate 6 and with discharge ports 5' of the underside of the housing 2".

As also seen in FIG. 15, discharge ports 5' on the underside of housing 2" are equipped with filtrate discharge fittings 32, which matingly engage with receptacles 25 of a micro titer plate 26.

Many variants of the basic inventive idea are contemplated. For example, it could be advantageous in certain embodiments to instead situate gasket 7 between membrane 15 and filtrate chamber 11. As mentioned above, devices according to the invention could be designed for use as a stackable tangential flow module useable singly or in series, as in the embodiments described with reference to FIGS. 1–8; or for use in a centrifuge, as in the embodiments described with reference to FIGS. 9–13. Gas or liquid pressure or vacuum may be used to provide the driving force to push or pull solvent and small micromolecules through the membrane. The gasket means could be positioned in a suitable seat around one or both of the two apertures.

The present invention provides great flexibility as to the selection of materials for the different components of the filtration module. Bonding compatibility is not necessary between any of the components. This means, for example, that a relatively soft and flexible material could used for filtration insert 1 or parts thereof, while a relatively rigid and strong material could be used for the sleeve housing 2". Gasket 7 could even be integrated into support plate 6 and/or upper plate 12 of the filtration insert. Gasket 7 could thus have the form of a ridge at the periphery of membrane support plate 6 and/or upper plate 12 and be formed from the same material as the rest of the parts 6 and 12.

The chemical properties of the different components could also be chosen with greater flexibility. A material with higher solvent-resistance could, for example, be chosen for the internal structure in contact with the liquid flow path.

The two sleeve parts 2, 2' have been shown with closed end portions. This design gives a very strong and rigid sleeve which is able to stand high pressures. But it should be understood that such closed end portions are not absolutely necessary in all applications.

A method for manufacturing the device according to the invention comprises the following steps: gasket means are first arranged around at least one of the apertures in the concentration chamber or the filtrate chamber. One of the apertures is then covered with a membrane with its feed side against the concentration chamber and its permeate side against the filtrate chamber. The chambers are then assembled with the apertures arranged over each other and a pressure-resistant sleeve is finally fitted on the outside and around the combination of the concentration chamber, the gasket means, the membrane and the filtration chamber. The sleeve will create and maintain a pressure sufficiently high to seal the membrane fluid-tight against at least one of the chambers during the assembly, while at the same time effecting an increase in the structural support of the entire assembly.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. Device for concentrating and/or purifying macromolecules in a liquid by filtration through a membrane comprising (a) a two-sided filtration insert comprising:
  (i) an upper plate having at least one concentration chamber adapted to receive and contain a liquid containing macromolecules to be processed, each of said at least one concentration chamber being provided with at least one first port that is separate from and in fluid communication with said concentration chamber;
  (ii) a membrane support plate having at least one filtrate chamber for supporting the permeate side of at least one membrane, said at least one filtrate chamber provided with at least one second port that is separate from and in fluid communication with said filtrate chamber and;
  (iii) at least one membrane having a feed side and a permeate side, said membrane being fluid-tight along its periphery and situated over at least one of said first and second ports and separating said at least one concentration chamber and said at least one filtrate chamber; and
  (iv) elastic gasket means arranged around at least one of said first and second ports and in contact with at least one side of said at least one membrane; and (b) a two-part pressure-resistant sleeve with closed end portions, said two-part sleeve being separate from said filtration insert and matingly engaging said upper plate and said membrane support plate of said filtration insert so as to surround said first and second ports, said two-part sleeve being sized so as to exert and maintain sufficient compressive forces to seal said at least one membrane fluid-tight against said concentration chamber and said filtrate chamber wherein said compressive forces arise solely from the engagement of said two-part sleeve with said upper plate and said membrane support plate.

2. The device of claim 1 wherein said gasket means is in the form of a ridge of elastic material and is integral with at least one of said concentration chamber and said filtrate chamber.

3. The device of claim 1 with a plurality of concentration and filtrate chambers in substantial alignment and adapted to receive and process a plurality of liquid samples.

4. The device of claim 3 adapted to matingly engage the receptacles of a micro titer plate.

* * * * *